United States Patent [19]

Lappalainen et al.

[11] Patent Number: 5,654,139
[45] Date of Patent: Aug. 5, 1997

[54] ALLELIC VARIATION OF THE SEROTONIN 5HT$_{2C}$ RECEPTOR

[75] Inventors: Jaakko Lappalainen; Markku Linnoila, both of Bethesda; David Goldman, Potomac, all of Md.

[73] Assignee: The United States of America as represented by the Department of Health and Human Services, Washington, D.C.

[21] Appl. No.: 310,271

[22] Filed: Sep. 21, 1994

[51] Int. Cl.⁶ .................. C12N 15/00; C12N 15/12
[52] U.S. Cl. .................. 435/6; 536/23.5; 536/24.3; 536/24.31; 536/24.33; 435/320.1; 435/334
[58] Field of Search .................. 536/23.1, 23.5, 536/24.3, 24.31, 24.33; 435/6, 172.3, 320.1, 240.1, 240.2

[56] References Cited

U.S. PATENT DOCUMENTS 4,985,352  1/1991  Julius et al. .................. 435/6

FOREIGN PATENT DOCUMENTS 2696749   4/1994  France.
WO9409130 4/1994  WIPO.

OTHER PUBLICATIONS

Humphrey et al., *Trends Pharmacol. Sci.* 14:233, 1993.
Saltzman et al., *Biochem. Biophys. Res. Commun.* 181:1469, 1991.
Baldwin, *Curr. Opin. Cell Biol.* 6:180, 1994.
Chanda et al., *Mol. Pharmacol.* 43:516, 1993.
Choudhary et al., *Mol. Pharmacol.* 43:755, 1993.
Foguet, M. et al., *Neuroreport* 3(4):345–48, 1992.
Lappalainen, J. et al., *American Journal of Human Genetics*, 55 (3 Suppl.), p. A156, Abstract 899, Oct. 1994.
Lappalainen et al., *Genamics*, 27(2):274–79, 1995.
Nielsen, D., et al., "Genetic Mapping of the Human Tryptophan Hydroxylase Gene on Chromosome II, Using an Intronic Conformational Polymorphism", *Am. J. Hum. Genet.*, 51:1366–1371, 1992.
Glavac, D, et al., "Optimization of the Single–Strand Conformation Polymorphism (SSCP) Technique for Detection of Point Mutations", *Human Mutation*, 2:404–414, 1993.

*Primary Examiner*—Marianne P. Allen
*Attorney, Agent, or Firm*—Knobbe, Martens, Olson & Bear

[57] ABSTRACT

We describe identification of a non-conservative amino acid substitution in the 5-HT$_{2C}$ receptor gene. The variant was found using single strand conformational polymorphism (SSCP) analysis. By typing this polymorphism in CEPH families, the gene was genetically mapped on the long arm of the X chromosome. Since this polymorphism was not detectable as a conventional RFLP, we also developed a PCR-RFLP based method which allows rapid genotyping in populations and families.

16 Claims, 4 Drawing Sheets

ALLELIC VARIATION OF THE SEROTONIN 5HT$_{2C}$ RECEPTOR

FIELD OF THE INVENTION

This invention relates to serotonin receptors. Specifically, this invention relates to allelic variants of the serotonin 5HT$_{2C}$ receptor.

BACKGROUND

Family, twin and adoption studies indicate genetic vulnerability to psychiatric disorders, including antisocial personality (Crowe, *Arch. Gen. Psychiatry* 31:785, 1974), suicidal behavior (Roy et al., *Arch. Gen. Psychiatry* 48:29, 1991), panic disorder and anxiety. Family and population studies have shown that these disorders usually co-occur with alcoholism and alcohol abuse (Roy et al., *Prog. Neuro-Psychopharmacol. Psychiatry* 11:173, 1987). Although psychiatric disorders often arise from a complex combination of environmental, genetic and biological factors, it may be possible to find biochemical and genetic variables that predict these behaviors and also facilitate implementation of preventative and therapeutic measures.

Several lines of evidence suggest that a lower activity of brain serotonergic pathways is related to several neuropsychiatric disorders. For example, lower levels of 5-hydroxyindoleacetic (5-HIAA), the main metabolite of serotonin (5-HT) in the cerebrospinal fluid (CSF) has been reported in clinical studies of aggression, depression, impulsive crime and alcoholism. In the genetic hypothesis of these disorders, vulnerability is transmitted through inheritance of a functionally divergent allele. Variation in central serotonin function would have pleiotropic effects beyond behavior. For example, some effects would be increasing the vulnerability to anxiety and mood disorders as well as impulsive/aggressive behaviors.

Several important genes for normal brain serotonin function have been cloned, including tryptophan hydroxylase (Stoll and Goldman, *J. Neurosci. Res.* 28:457, 1991), serotonin transporter (Hoffman et al., *Science* 254:579, 1991) monoamine oxidases A and B (Bach et al., *Proc. Natl. Acad. Sci. USA* 85:4934, 1988) and several serotonin receptors (Humphrey et al., *Trends Pharmacol. Sci.* 14:233, 1993).

Serotonin acts in vivo by binding to specific receptors located in the central nervous system. A vast array of serotonin receptors has already been discovered. Investigators have divided the serotonin receptor subtypes into four pharmacologically distinct classes designated 5-HT$_1$ to 5-HT$_4$. The 5HT$_1$ subcategory contains five different subtypes referred to as 5HT$_{1A-E}$. The 5-HT$_2$ receptors can be divided into three subclasses, 5-HT$_{2A}$, 5-HT$_{2B}$ and 5-HT$_{2C}$. The primary structures for a number of these receptors have been elucidated by molecular cloning, including the 5-HT$_1$, 5-HT$_2$ and 5HT$_3$ subclasses.

Serotonin receptor agonist and antagonists have been developed as drugs for treating specific neuropsychiatric disorders. Drugs with affinity for 5-HT$_2$ receptors are used to treat schizophrenia, Parkinsonism, and anxiety disorders. Several azapirones, such as buspirone, gepirone, and ipsapirone, have high affinities for 5HT$_{1A}$ receptors in the brain, and are used to treat anxiety. For example, clozapine which is an antipsychotic drug with fewer extrapyramidal side effects is used to treat schizophrenic patients who do not respond to other drug treatments. Clozapine has a strong affinity for the serotonin 5-HT$_2$ subclass of receptors. In addition, 5-HT$_{1A}$ class agonists, such as buspirone, are effective treatments for anxiety.

Highly selective 5-HT uptake inhibitors, which have minimal effects on norepinephrine or dopamine uptake or on other neurotransmitter receptors, have been used successfully to treat depression. Naturally, characterizing all of the specific 5-HT receptors would clarify the role of serotonin in the central nervous system, and assist neuropsychiatric drug development.

The 5-HT$_{2C}$ serotonin receptor subtype has been particularly interesting to investigators searching for the molecular bases of neuropsychiatric disorders. The 5-HT$_{2C}$ receptor gene is widely expressed in the brain where it is involved in regulating endocrine responses. Particular responses include the production and secretion of adrenocorticotropic hormone (ACTH), oxytocin and prolactin. Genes for rat, mouse and human (Saltzman et al., *Biochem. Biophys. Res. Commun.* 181:1469, 1991) 5-HT$_{2C}$ receptors have been cloned. The functional state of 5-HT$_{2C}$ receptors in normal controls and various patient groups has been studied in vivo by administering mCPP, a non-selective 5-HT$_{2C}$ agonist, and measuring hormonal and psychological responses. In alcoholism, panic disorder, seasonal affective disorder and obsessive-compulsive disorder, mCPP has been shown to induce different hormonal and psychological responses in patients and controls.

As discussed, several lines of evidence suggest abnormal function of serotonin receptors in certain neuropsychiatric disorders. Specifically, pharmacological studies in humans suggest that abnormal function of 5-HT$_{2C}$ receptors play a role in the etiology of certain disorders. Accordingly, there is a need to identify and characterize the serotonin receptors and those functional variants which associate with neuropsychiatric disorders. There is a corresponding need for assays that will permit identification of functional variants in various segments of the population. With this knowledge, receptor variant-specific drugs and diagnostic information can be developed.

BRIEF DESCRIPTION OF THE FIGURES

FIG. 1A corresponds to the human 5-HT$_{2Ccys}$ receptor. FIG. 1B corresponds to the human 5-HT$_{2Cser}$ receptors. The X-axis represents the amino acid number of the human 5-HT$_{2C}$ receptor.

SUMMARY

Figure 1A:
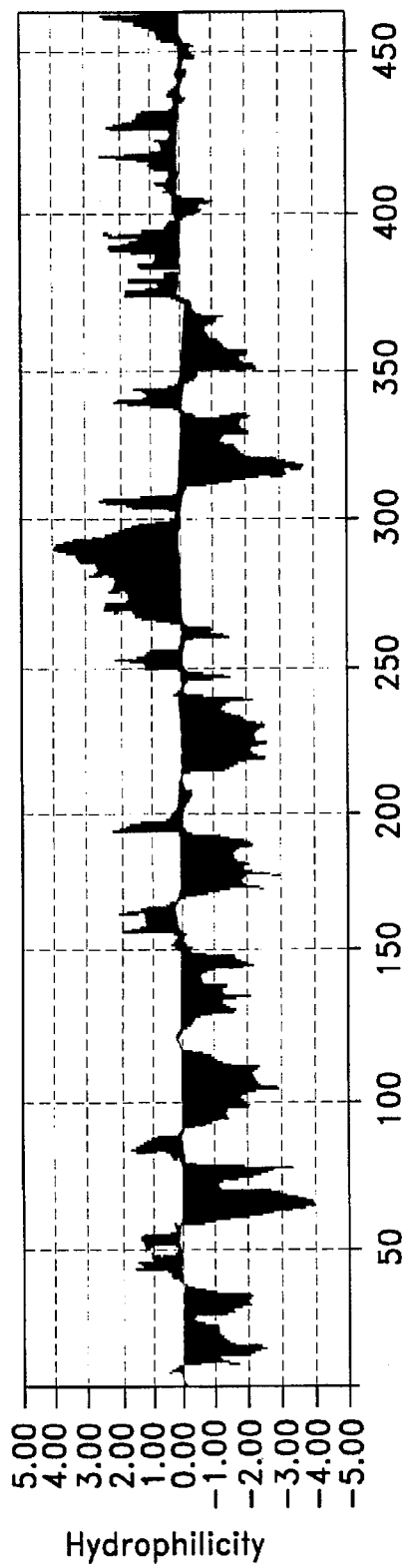
FIGS. 1A–B is a set of hydrophilicity plots.

Central to the present invention is the discovery of an allelic variant of the serotonin 5HT2C receptor that is functionally different from the predominant wild-type receptor. One embodiment of the present invention relates to isolated DNA encoding that serotonin 5HT2C receptor wherein the DNA encodes a serine at amino acid position 23 of the receptor. The isolated DNA may, for example, be provided in a recombinant vector. Preferably the isolated DNA has the nucleic acid sequence of SEQ ID NO:1.

Also contemplated in the present invention is an isolated protein having the amino acid sequence of a serotonin 5HT$_2$C receptor, wherein the protein has a serine residue at amino acid position 23. Preferably, the protein has the amino acid sequence of SEQ ID NO:2.

Assays for the variant serotonin receptor have significant value, both in research relating to serotonin function and in diagnostic assays because of the correlation between behavioral disorders and this receptor. Thus, the invention includes a method for detecting the presence of DNA encoding an allelic variant of the serotonin 5HT2C receptor, comprising isolating DNA encoding the serotonin 5HT2C receptor, amplifying a region of the DNA that encodes amino acid number 23 of the serotonin 5HT2C receptor, and determining whether the isolated DNA encodes a serine residue at amino acid number 23, wherein a serine residue at amino acid position 23 indicates the presence of the allelic variant of the serotonin 5HT2C receptor. In one embodiment, the amplifying step comprises polymerase chain reaction amplification. This amplifying step may advantageously use DNA primers that insert a new restriction site near the codon that encodes amino acid number 23. For example, in one embodiment, the restriction site is cleaved by HinfI. In a particular exemplification, the DNA primers are SEQ ID NOS 5 and 6. The determining step of the assay may advantageously be restriction enzyme digestion followed by gel electrophoresis, and may optionally include denaturation of the isolated DNA. One suitable restriction enzyme is Rsa I. A preferred gel electrophoresis utilizes a Mutation Detection Enhancement gel. In another embodiment, the determining step further comprises nucleic acid sequencing of the amplified DNA.

The present invention further includes antibody specific for the serotonin 5HT2C allelic variant receptor protein wherein the receptor protein has a serine at amino acid position 23. This antibody does not bind the predominant wild-type receptor. Advantageously, the antibody is a monoclonal antibody.

These antibodies, in turn, provide a method for detecting the presence of an allelic variant of the serotonin HT2C receptor, comprising providing a biological sample containing the serotonin 5HT2C receptor, contacting the sample with an antibody which specifically binds to a serotonin 5HT2C receptor with a serine residue located at amino acid position 23, and detecting the binding of the antibody to the receptor, wherein detectable binding indicates the presence of an allelic form of the serotonin 5HT2C receptor. Preferably, the cells are human, and may be brain cells. It is preferred that the monoclonal or polyclonal antibody is specific for the extracellular loop of the first transmembrane domain of the serotonin 5HT$_2$C receptor. Labeled antibody is particularly useful, including radiolabeled antibody and fluorescent antibody. With fluorescent antibody, the detecting step can comprise fluorescence activated cell sorting.

The present invention also includes a method for detecting the presence of an allelic variant of the serotonin 5HT2C receptor by 1) providing a biological sample containing the serotonin 5HT$_2$C receptor; 2) contacting the sample with an antibody which specifically binds to a serotonin 5HT$_2$C receptor having a cysteine residue located at amino acid position 23, and wherein said antibody does not bind a 5HT$_2$C receptor having a serine residue at position 23; 3) detecting the absence of binding of said antibody to said receptor, wherein lack of detectable binding indicates the presence of an allelic form of the serotonin 5HT2C receptor.

DETAILED DESCRIPTION

Figure 1B:
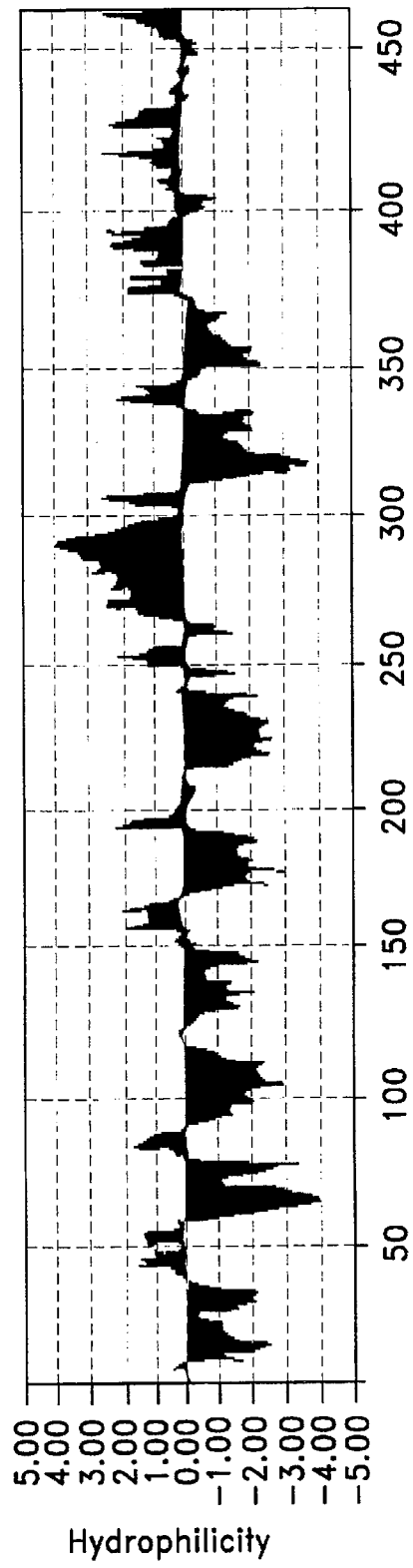

We have discovered an allelic variant of the 5-HT$_2$C receptor. This variant is identical to the wildtype 5-HT$_2$C receptor except for a non-conservative amino acid change in the extracellular portion of the first putative transmembrane domain. A substitution of a serine in place of the normal cysteine occurred in the 23rd amino acid of the final protein. A guanine (G) to cytosine (C) genetic transversion caused a cysteine to be replaced by serine at amino acid 23. As this change places a hydrophilic amino acid in a hydrophobic domain (see FIG. 1), it would be expected to alter the configuration of the membrane-bound receptor.

Previously, single amino acid substitutions within the 2nd, 3th, 5th, and 7th transmembrane domains of various serotonin receptors have been shown to drastically change the ligand binding characteristics (Baldwin, Curr. Opin. Cell Biol. 6:180, 1994; Chanda et al., Mol. Pharmacol. 43:516, 1993; Choudhary et al., Mol. Pharmacol. 43:755, 1993). In addition, the cysteine at position 23 may be linked to another cysteine residue in the wildtype protein forming a di-sulphide bond bridge. This possibility further suggests that the variant protein, designated 5-HT$_{2Cser}$, is conformationally and functionally different from the wildtype protein.

The present invention includes our discovery of the 5-HT$_{2Cser}$ gene (SEQ ID NO:1) along with the corresponding variant protein product (SEQ ID NO:2) of this gene. In addition, antibodies that can distinguish between the two 5-HT$_2$C forms are anticipated.

One of ordinary skill in the art will appreciate that a kit can be produced that contains all the necessary components to identify a carrier of the HT$_{2Cser}$ gene. This kit would include PCR primers, PCR enzymes, restriction enzymes and any other component useful for determining the one base pair change between the wildtype gene and the allelic variant. PCR primers could be those exemplified below and in SEQ ID NOS: 3 and 4, or constructed by those of ordinary skill in the art as described below.

It should also be appreciated that one could identify the nucleic acid change between the wildtype and the variant 5-HT$_2$C receptor by well known hybridization techniques. Under known conditions, a one base pair mismatch can be determined by, for example, Southern blot analysis or in situ hybridization.

Through chromosomal mapping studies we have discovered that 5-HT$_{2Cser}$ is located on the X-chromosome (see FIG. 5). It is important to recognize that since 5-HT$_{2C\ ser}$ is located on the X-chromosome, any associated diseases should have an X-linked component.

We identified the 5-HT$_{2Cser}$ polymorphism by amplifying genomic DNA from 62 individuals and performing single strand conformational polymorphism (SSCP) analysis. This procedure is a rapid and efficacious method for detecting polymorphisms (Dean et al., Cell 61:863, 1990; Glavac and Dean, Hum. Mutation 2:404, 1993; Poduslo et al., Am. J. Hum. Genet. 49:106, 1992). Although 90% of the 5-HT$_2$C receptor coding region was screened for sequence variants, no other variants were detected. We found that the 5-HT$_{2Cser}$ variant was a relatively common non-conservative amino acid substitution. In a random population sample, the allele frequency of the 5-HT$_{2Cser}$ gene was 13 percent.

Because the polymorphism was not detectable as a conventional restriction fragment length polymorphism (RFLP), we used a PCR primer which introduced a base substitution close to the codon of interest to create an artificial HinfI restriction site in only one of the two allelic forms (Haliassos et al., *Nuc. Acid Res.* 17:3606, 1989). This protocol is discussed in more detail below. Digestion with HinfI yielded two fragments (18 bp and 86 bp) with the 5-HT$_{2Cser}$ gene but left the DNA product undigested (104 bp) with the wildtype 5-HT$_{2Ccys}$ gene. This method is known as the PCR-RFLP method.

As both the SSCP and PCR-RFLP methods can detect the single nucleotide difference between the two serotonin receptor alleles, both methods will yield identical results when genotyping any particular individual. Genotyping 50 individuals using both the PCR-RFLP and SSCP analyses yielded identical results, demonstrating reproducibility of these methods. The conversion of the SSCP-detected variant to a RFLP site facilitates genotyping, makes the genotyping more accessible to a variety of laboratories (e.g., research and clinical diagnostic laboratories), and confirms the sequencing results (see below). This is especially important when PCR products are directly sequenced using cycle sequencing.

A tight linkage was found between the described 5-HT$_{2C}$ receptor polymorphism and a marker located on the human X chromosome, DXS734. The DXS734 marker has previously been placed in the Xq21.1 region. Also, positive lod-scores were obtained using a number of other markers in the Xq21.1 region (see TABLE 1).

The Xq21.1 region is interesting because it contains a number of genes that have been correlated with clinical conditions manifested with mental retardation. These diseases include choroideremia, Allan-Herndon-Dudley syndrome, Miles-Carpenter syndromes, MRX7 and MRX8. Therefore, this 5-HT$_{2C}$ receptor is a potential candidate for these syndromes.

The present invention, thus, includes isolated or purified 5-HT$_{2Cser}$ receptor; DNA encoding that receptor; antibodies with specific binding to the 5-HT$_{2Cser}$ receptor and assays for detecting the receptor. In addition, expression vectors encoding 5-HT$_{2Cser}$ and cells expressing the recombinant expression vector are also anticipated. Further, kits and assays for determining the presence or absence of the variant receptor are a part of the present invention. Thee is an established need for assays useful in correlating behavioral patterns with chemical differences in individuals, and such an assay for the present 5HT variant will be a valuable tool in neuropsychiatric investigations. The isolated or purified protein is useful, inter alia, in competitive assays and in preparation of monoclonal and polyclonal antibody against the variant receptor. An additional facet of the present invention is provision of assays for compounds that bind or block binding to the 5-HT$_{2Cser}$ receptor. Each of these embodiments is discussed in more detail in the following examples.

As discussed above, a strong correlation exists between the serotonin family of receptors and some neuropsychiatric diseases. For this reason it is important to identify as many of the serotonin receptor variants as possible. Investigators looking for drugs that affect the quantity of serotonin byproducts need to have methods for testing their candidates against all serotonin receptors. Thus, the 5-HT$_{2Cser}$ variant and associated DNA and assays provide important investigative tools for both behavioral research and the screening of neuropsychiatric drug candidates.

Another application of our discovery is screening individual carriers of the variant gene. Correlations between the allelic variant and neuropsychiatric disorders lead to the necessity of providing screening techniques for identifying carriers of the variant allele.

As a first step we analyzed the 5-HT$_{2C}$ receptor gene for variants in a population of alcoholics.

EXAMPLE 1

Detection of the 5-HT$_{2Cser}$ Variant Allele in Violent Alcoholics Using the Single-Strand Conformation Polymorphism (SSCP) Method Cell lines were derived from individual patients by immortalizing lyphoblastoid cells with Epstein Barr virus. The populations included Finnish alcoholic violent offenders (n=16), Finnish alcoholic arsonists (n=5) with low CSF 5-HIAA concentrations, alcoholic American Indians (Jemez Pueblo n=8, Cheyenne n=2) and U.S. alcoholic male Caucasians (n=16). DNA samples were taken from these immortalized cell lines using standard protocols. Each genomic DNA sample was amplified in the exon 2 portion of the 5-HT$_{2C}$ receptor gene by using the polymerase chain reaction (PCR) with primers that border the exon 2 region: 5HT2C7 (5' CACCTAATTGGCCTATTGGTT 3') (SEQ ID NO:3) and 5HT2C8 (5' AAGGATTGCCAGGAGAGACAG 3') (SEQ ID NO:4). Using these two primers will allow amplification of the region encoding exon 2 of the gene. Although these primers were used to amplify the region of interest, it will be appreciated by those skilled in the art that other primers could accomplish the same result.

Amplification was performed in 7.5 μl reactions consisting of 30 ng of DNA, 0.25 μM of each primer, 250 μM each of dATP, dCTP, dGTP, dTTP, 1 μCi of [α$^{32}$P] dCTP, 50 mM KCl, 1.5 mM MgCl$_2$, 0.001% gelatin, 10 mM Tris-HCl (pH 8.3) and 0.75 units of Taq DNA polymerase (AmpliTaq from Perkin Elmer Cetus).

DNA samples were amplified for 30 cycles, each consisting of 1 min at 95° C., 2 min at 55° C. and 3 min at 72° C. After amplification, the radioactively labeled amplified DNA was digested with 5 units of restriction enzyme Rsa I under standard conditions to allow this enzyme to generate smaller DNA fragments to increase the sensitivity of SSCP detection.

Following digestion, the DNA was denatured by diluting the reaction mixture with 15 μl of 95% formamide, 10mM NaOH, 0.05% xylene cylanol and 0.05% bromophenol blue, and incubating at 95° C. for 3 min followed by chilling on ice.

We loaded 4 μl of each denatured DNA sample onto a Mutation Detection Enhancement (MDE) gel (AT Biochem, Malvern, Pa.). The DNA was electrophoresed at 4° C. for 16 hr at 6 V. MDE gels contain polyvinyl and are suggested to be superior to acrylamide gels in sensitivity for detecting small mutational differences between DNA sequences. The MBE gel was dried and autoradiography was performed at −70° C. DNA fragments containing a single nucleotide difference were detected by their different relative rates of electrophoretic migration on this gel.

To provide an additional assay for determining carriers of the 5-HT$_{2Cser}$ variant, we performed nucleic acid sequencing reactions of the amplified PCR fragments described above. However, one of ordinary skill in the art will appreciate that many ways are available to directly determine the nucleic acid sequence of DNA fragments.

EXAMPLE 2

DNA Sequence Determination of PCR DNA Products to Identify the 5-HT$_{2Cser}$ Variant Allele The PCR product was purified by agarose gel electrophoresis followed by extraction with glass beads (Geneclean, BIO 101, La Jolla, Calif.). DNA was directly sequenced by dideoxy cycle-sequencing according to the manufacturers' instructions (Life Technologies, Gaithersburg, Md.).

A G to C transversion caused a cysteine (encoded by TGT) to be replaced by serine (encoded by TCT) at amino acid position 23. These sequences were determined from two males with the 5-$HT_{2Ccys}$ genotype, one male with the 5-$HT_{2Cser}$ genotype and a female who is heterozygous for the 5-$HT_{2Ccys}$/5-$HT_{2Cser}$ genotypes.

The sequence establishes the molecular basis for the genetic polymorphism detected using the methods described in Example 1. Furthermore, the amino acid substitution encoded by the variant DNA sequence establishes that the 5-$HT_{2C}$ variant receptor protein has a serine at position 23 which may be physiologically significant. Also, the particular DNA sequence of the variant 5-$HT_{2Cser}$ allele facilitated development of another, technically easier assay, called PCR-RFLP (described in Example 4), for determining the genotype of different individuals.

Having discovered the polymorphism, we then determined the chromosomal location of this gene as described below in Example 3.

EXAMPLE 3

Genetic Mapping of the 5-$HT_{2C}$ Receptor (HTR2C)

The 5-$HT_{2C}$ genotype was determined in 10 informative CEPH families. Data were entered into programs provided by CEPH, and files with X chromosome markers were prepared. Two-point lod score analysis was performed using LINKAGE (Lathrop et al., *Proc. Natl. Acad. Sci. USA* 81:3443, 1984) and MAPMAKER (Lander et al., *Genomics* 1:174, 1987), and the two-point values were utilized for multipoint analysis. Multipoint linkage analysis was performed using markers that showed the lowest recombination fraction. Also, other highly informative markers were chosen from both the Genethon (Weissenbach et al., *Nature* 359:794, 1992) and NIH/CEPH consortium maps (*Science* 258:67, 1992). The 5-$HT_{2C}$ gene was placed in all positions of a map of markers ordered with greater than 1000:1 odds, using the TRY command of MAPMAKER The data analyzed in this manner for a number of genetic markers is presented in TABLE 1.

Figure 2:
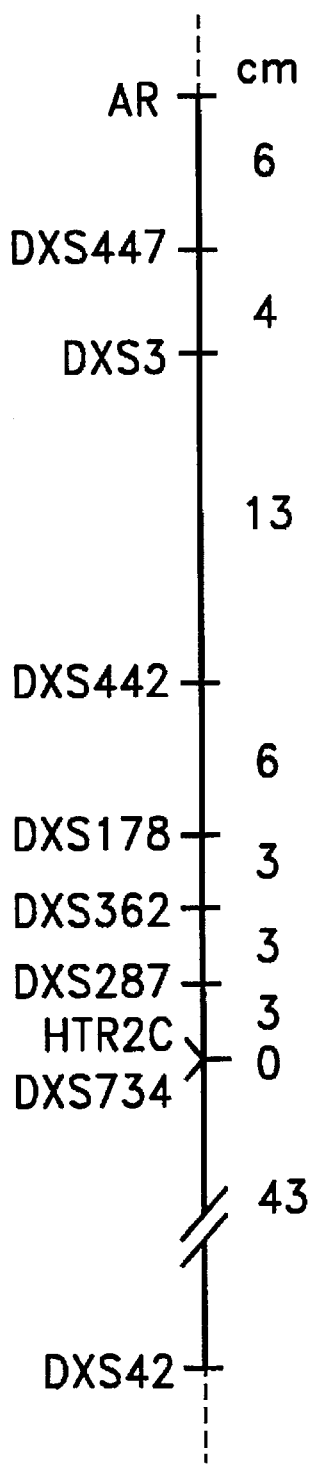
FIG. 2 is a diagram showing the genetic location of human 5-HT$_{2C}$ receptor gene (HTR2C). Multipoint analysis placed the 5-HT$_{2C}$ gene on the long arm of the X chromosome and in the interval between DXS362 and DXS42 with odds greater than 1000:1. Sex averaged intervals between the HTR2C gene locus and markers are shown.

The 5-$HT_{2C}$ receptor polymorphism was found to segregate in an X-linked codominant fashion in CEPH families and the genotypes for 10 informative families were determined. Allele frequencies in 47 unrelated caucasians (CEPH parents) were 0.13 and 0.87 for 5-$HT_{2Cser}$ and 5-$HT_{2Ccys}$, respectively. Using these same families, the gene was mapped by using two-point lod scores (TABLE 1 shows the maximum scores). Two-point analysis yielded a maximum lod-score of 10.22 to DXS734 which has previously been assigned to Xq21.1. There were also a number of other markers in this region which were linked to the 5-$HT_{2C}$ receptor gene. Multipoint analysis placed the 5-$HT_{2C}$ gene on the long arm of X chromosome and in the interval between DXS362 and DXS42 with odds greater than 1000:1. Sex averaged intervals between the 5-$HT_{2C}$ gene locus and markers are shown in FIG. 2.

TABLE 1

Markers linked to HTR2C

| Locus | Probe | Enzyme | Location | q | Zmax |
|---|---|---|---|---|---|
| DXS1001 | 248we5 | (AC)n | X | 8.6 | 3.67 |
|  | 454 | GT | Xq | 18.0 | 3.05 |
|  | 458 | GT | Xq | 19.0 | 3.51 |
| DXS329 | KZO-7 | HindIII | Xq24-q26 | 6.2 | 3.19 |
| DXS328 | QST-13 | HindIII | Xq21.3-q22.1 | 12.2 | 5.14 |
| DXS328 | QST-47 | HindIII | Xq21.3-q22.1 | 11.6 | 3.49 |
| DXS327 | QST-7 | MspI | Xq21.2-q22.1 | 5.0 | 3.69 |
| DXS350 | RX-100M1 | MspI | Xq21.1-q24 | 0.0 | 4.51 |
| DXS350 | RX-100M2 | MspI | Xq21.1-q24 | 0.0 | 5.71 |
| DXS358 | RX-187 | HindIII | Xq24-qter | 0.0 | 7.22 |
| DXS358 | RX-187A | TaqI | Xq24-qter | 0.0 | 6.01 |
| DXS358 | RX-187B | TaqI | Xq24-qter | 0.0 | 4.21 |
| DXS362 | RX-237 | MspI | Xq21.1-qter | 2.7 | 8.24 |
| DXS362 | RX-237 | TaqI | Xq21.1-qter | 8.1 | 6.01 |
| DXS366 | RX-329 | TaqI | Xq21.1-q24 | 0.0 | 3.31 |
| DXS447 | RX-404 | BglII | Xq21.1 | 13.8 | 3.38 |
| DXS734 | RX-99 | TaqI | Xq21.1 | 0.0 | 10.22 |
| DXS456 | XG30B | PCR | Xq21-q22 | 7.5 | 4.73 |
|  | chil6 | HindIII | X | 14.2 | 4.56 |
| DXS3 | P19-2 | MspI | Xq21.3 | 9.5 | 3.15 |

The DXS markers are anonymous loci. "Enzyme" refers to the enzyme that detects the polymorphism; "(AC)n" and "GT" represent CA/GT dinucleotide repeat loci; "Location" is the known physical location of the marker on the X chromosome. "q" is the sex-averaged recombination frequency observed with 5HT2C and "Zmax" is the LOD (log of odds) score at the value of the recombination frequency.

These results mapped the 5-$HT_{2C}$ receptor gene to a small portion of the long arm of the X chromosome which is genetically linked to a variety of known mental retardation syndromes such as choroideremia, Allan-Herndon-Dudley syndrome, Miles-Carpenter syndromes, MRX7 and MRX8. Thus, the described 5-$HT_{2C}$ genetic polymorphism could be useful in diagnosis of mental retardation syndromes.

We also development a technically easier assay, called PCR-RFLP, for determining the genotype of different individuals.

EXAMPLE 4

Detection of the 5-$HT_{2Cser}$ Variant Allele in Individuals by Using the PCR-RFLP Method A 104 bp region of the 5-$HT_{2C}$ receptor gene near the polymorphism was amplified using a second set of PCR primers. One of the PCR primers was used to introduce a base substitution close to the codon which differs in the 5-$HT_{2Cser}$ variant allele, creating an artificial HinfI restriction site only in the amplified DNA corresponding to the 5-$HT_{2Cser}$ variant allele (Haliassos et al., *Nuc. Acid Res.* 17:3606, 1989).

The PCR primers were REPA1 (5' TTGGCCTATTG-GTTTGGGAAT 3') (SEQ ID NO:5) and ARTIFACT2 (5' GTCTGGGAATTTGAAGCGTCCAC 3') (SEQ ID NO:6). REPA1 introduces a C to G substitution 4 bp upstream from the polymorphic site. This substitution artificially creates a HinfI RFLP. That is, when DNA containing the 5HT$_{2Cser}$ allele is amplified using these primers and then digested with HinfI, it yields two fragments (18 bp and 86 bp). These fragments can be detected by commonly used gel electrophoresis.

In contrast, when DNA containing the more common 5-$HT_{2Ccys}$ allele was similarly amplified and treated with HinfI, the amplification product remained undigested and was seen as a single band (104 bp) following gel electrophoresis. Amplification products were visualized in ethidium bromide stained 10% polyacrylamide gels. In this study, we amplified the DNA from a population including a total of 50 controls and patients with psychiatric disorders.

Amplification was performed using 60 ng of DNA, 0.25 µM of each primer, 250 µM each of dATP, dCTP, dGTP, dTTP, 50 mM KCl, 1.5mM MgCl$_2$, 0.001% gelatin, 10 mM Tris-HCl (pH 8.3) and 0.75 units of AmpliTaq (Perkin Elmer Cetus) in a total volume of 15 µl. Samples were amplified for 35 cycles, each consisting of 1 min at 95° C., 2 min at 50° C. 3 min at 72° C.

After amplification, 10 units of HinfI (New England Biolabs) and recommended buffer (1×concentration with respect to the final volume) were added directly to PCR samples and incubated for 10 h at 37° C. The DNA fragments were resolved by 10% polyacrylamide gel electrophoresis and stained with ethidium bromide.

To check the accuracy of the PCR-RFLP method, we performed the SSCP method on the same 50 people, including patients and controls, as those used for the PCR-RFLP experiment. We found that both the SSCP method and the PCR-RFLP method detected the same allelic variant in the 5-HT$_{2C}$ receptor gene. For this reason, both methods should be equally reliable in typing individuals for their respective 5-HT$_{2C}$ receptor allele(s). Note that because the 5-HT$_{2C}$ receptor gene is located on the X chromosome (see Example 3), generally males will carry only one allele. However, females can be either homozygous or heterozygous for these two alleles.

The PCR-RFLP method is technically easier than the SSCP method because it does not require radioactive labeling of the amplified DNA. In the PCR-RFLP method, amplified DNA fragments are detected by electrophoresis through a gel without requiring denaturation of the DNA. Thus the PCR-RFLP method allows rapid genotyping of populations and families.

Having determined the relative frequencies of the two identified forms of the 5-HT$_{2C}$ receptor in a normal population using the PCR-RFLP method, we determined whether these alleles occur at abnormal frequencies in subpopulations exhibiting several neuropsychiatric disorders.

EXAMPLE 5

Detection of the 5-HT$_{2Cser}$ Variant Allele in Finnish Alcoholic Violent Offenders Using the SSCP and PCR-RFLP methods described above, we isolated DNA from immortalized cells derived from Finnish alcoholic violent individuals. Subjects were further classified whether they fulfilled the DSM III criteria for antisocial personality disorder (APD), intermittent explosive disorder (IED), or other DSM III diagnoses. In addition, we took DNA from cell lines of controls that had been psychologically interviewed and determined to be mentally healthy. TABLE 2 shows the results of this experiment.

TABLE 2

5-HT$_{2C}$ Genotype Frequencies in Alcoholic Violent Offenders and Controls

| | 5-HT$_{2Ccys}$ | 5-HT$_{2Cser}$ | # Subjects |
| --- | --- | --- | --- |
| ASP | 0.86 | 0.14 | 72 |
| IED | 0.92 | 0.08 | 38 |
| Other offenders | 0.95 | 0.05 | 37 |

TABLE 2-continued

5-HT$_{2C}$ Genotype Frequencies in Alcoholic Violent Offenders and Controls

| | 5-HT$_{2Ccys}$ | 5-HT$_{2Cser}$ | # Subjects |
| --- | --- | --- | --- |
| All offenders | 0.90 | 0.10 | 147 |
| Controls | 0.82 | 0.18 | 123 |

To determine if the 5-HT$_{2Cser}$ variant allele is linked to other neuropsychiatric disorders, a similar analysis is done using a subpopulation exhibiting suicidal behavior.

EXAMPLE 6

Detection of the 5-HT$_{2Cser}$ Variant Allele in Individuals Exhibiting Suicidal Behavior by Using the SSCP Method Using the SSCP method described in Example 1, genomic DNA isolated from suicidal individuals is analyzed for the frequency of the 5-HT$_{2Cser}$ allele. Because suicidal behavior has been shown to have a genetic component, the frequency of this allele is determined in the subpopulation exhibiting suicidal tendencies or behavior compared to a normal population. A correlation is found between the patients carrying the allelic variant of the 5-HT$_{2C}$ receptor and individuals exhibiting suicidal behavior.

To determine if the 5-HT$_{2Cser}$ variant allele is linked to other neuropsychiatric disorders, a similar analysis is done using subpopulations exhibiting panic disorder and clinical anxiety.

EXAMPLE 7

Detection of the 5-HT$_{2Cser}$ Variant Allele in Individuals Exhibiting Panic Disorder and/or Anxiety by Using the SSCP Method Using the SSCP method described in Example 1, genomic DNA isolated from individuals exhibiting panic disorder or clinical anxiety is analyzed for the frequency of the 5-HT$_{2Cser}$ allele. Because panic disorder and clinical anxiety have been shown to have a genetic component, the frequency of this allele is determined in the subpopulation exhibiting panic disorder and/or anxiety compared to a normal population. A correlation is found between the patients carrying the allelic variant of the 5-HT$_{2C}$ receptor and individuals exhibiting panic disorder and/or clinical anxiety.

To determine if the 5-HT$_{2Cser}$ variant allele is linked to other neuropsychiatric disorders, a similar analysis is done using a subpopulation exhibiting seasonal affective disorder.

EXAMPLE 8

Detection of the 5-HT$_{2Cser}$ Variant Allele in Individuals Exhibiting Seasonal Affective Disorder by Using the SSCP Method Using the SSCP method described in Example 1, genomic DNA isolated from individuals exhibiting seasonal affective disorder is analyzed for the frequency of the 5-HT$_{2Cser}$ allele. Because seasonal affective disorder has been shown to have a genetic component, the frequency of this allele is determined in the subpopulation exhibiting seasonal affective disorder compared to a normal population. A correlation is found between the patients carrying the allelic variant of the 5-HT$_{2C}$ receptor and individuals exhibiting seasonal affective disorder.

To determine if the 5-HT$_{2Cser}$ variant allele is linked to other neuropsychiatric disorders, a similar analysis is done using a subpopulation exhibiting obsessive-compulsive disorder.

EXAMPLE 9

Detection of the 5-HT$_{2Cser}$ Variant Allele in Individuals Exhibiting Obsessive-Compulsive Disorder by Using the SSCP Method Using the SSCP method described in Example 1, genomic DNA isolated from individuals exhibiting obsessive-compulsive disorder is analyzed for the frequency of the 5-HT$_{2Cser}$ allele. Because obsessive-compulsive disorder has been shown to have a genetic component, the frequency of this allele is determined in the subpopulation exhibiting obsessive-compulsive disorder compared to a normal population. To confirm the results obtained using the SSCP method, the PCR-RFLP method is also used on the sample from each individual.

To determine if the 5-HT$_{2Cser}$ variant allele is linked to other neuropsychiatric disorders, a similar analysis is done using a subpopulation having eating disorders.

EXAMPLE 10

Detection of the 5-HT$_{2Cser}$ Variant Allele in Individuals with Eating Disorders by Using the PCR-RFLP Method Using the PCR-RFLP method described above, genomic DNA isolated from individuals with eating disorders is analyzed for the frequency of the 5-HT$_{2Cser}$ allele. Because eating disorders have been shown to have a genetic component, the frequency of this allele is determined in the subpopulation exhibiting eating disorders compared to a normal population.

To determine if the 5-HT$_{2Cser}$ variant allele is linked to other neuropsychiatric disorders, a similar analysis is done using a subpopulation exhibiting schizophrenia.

EXAMPLE 11

Detection of the 5-HT$_{2Cser}$ Variant Allele in Individuals Exhibiting Schizophrenia by Using the PCR-RFLP Method Using the PCR-RFLP method described above, genomic DNA isolated from schizophrenic individuals is analyzed for the frequency of the 5-HT$_{2Cser}$ allele. Because schizophrenic behavior has been shown to have a genetic component, the frequency of this allele is determined in the subpopulation exhibiting schizophrenic tendencies or behavior compared to a normal population.

To determine if the 5-HT$_{2Cser}$ variant allele is linked to other neuropsychiatric disorders, a similar analysis is done using subpopulations exhibiting myoclonic disorders.

EXAMPLE 12

Detection of the 5-HT$_{2Cser}$ Variant Allele in Individuals Exhibiting Myoclonic Disorders by Using the PCR-RFLP Method Using the PCR-RFLP method described above, genomic DNA isolated from individuals exhibiting myoclonic disorder is analyzed for the frequency of the 5-HT$_{2Cser}$ allele. Because myoclonic disorder has been shown to have a genetic component, the frequency of this allele is determined in the subpopulation exhibiting myoclonic disorder compared to a normal population.

To determine if the 5-HT$_{2Cser}$ variant allele is linked to other neuropsychiatric disorders, a similar analysis is done using a subpopulation with epilepsy.

EXAMPLE 13

Detection of the 5-HT$_{2Cser}$ Variant Allele in Individuals with Epilepsy by Using the PCR-RFLP Method Using the PCR-RFLP method described above, genomic DNA isolated from individuals having epilepsy is analyzed for the frequency of the 5-HT$_{2Cser}$ allele. Because epilepsy has been shown to have a genetic component, the frequency of this allele is determined in the subpopulation exhibiting epilepsy compared to a normal population.

To determine if the 5-HT$_{2Cser}$ variant allele is linked to other disorders, a similar analysis is done using a subpopulation exhibiting manic-depressive illness.

EXAMPLE 14

Detection of the 5-HT$_{2Cser}$ Variant Allele in Individuals Exhibiting Manic-Depressive Illness by Using the PCR-RFLP Method Using the PCR-RFLP method described above, genomic DNA isolated from individuals exhibiting manic-depressive illness is analyzed for the frequency of the 5-HT$_{2Cser}$ allele. Because manic-depressive illness has been shown to have a genetic component, the frequency of this allele is determined in the subpopulation exhibiting manic-depressive illness compared to a normal population.

EXAMPLE 15

Detection of the 5-HT$_{2Cser}$ Variant Allele in Individuals Exhibiting Type I or Type II Alcoholism by Using the PCR-RFLP Method Using the PCR-RFLP method described above, genomic DNA isolated from individuals exhibiting Type I or Type II alcoholism is analyzed for the frequency of the 5-HT$_{2Cser}$ allele. Because Type I and Type II alcoholism have been shown to have a genetic component, the frequency of this allele is determined in the subpopulation exhibiting Type I or Type II alcoholism compared to a normal population.

EXAMPLE 16

Detection of the 5-HT$_{2Cser}$ Variant Allele in Individuals Exhibiting Mental Retardation Associated with the Xg21.1 Chromosomal Region by Using the PCR-RFLP Method The Xq21.1 region contains a number of genes that have been correlated with clinical conditions manifested with mental retardation including choroideremia, Allan-Herndon-Dudley syndrome, Miles-Carpenter syndromes, MRX7 and MRX8. Using the PCR-RFLP method described above, genomic DNA is isolated from individuals exhibiting one of these forms of mental retardation and analyzed for the frequency of the 5-HT$_{2Cser}$ allele. The frequency of this allele is determined in the subpopulation exhibiting Xq21.1-linked mental retardation compared to a normal population.

EXAMPLE 17

Production of Antibodies Against the 5-HT$_{2Cser}$ Variant Receptor Protein

Cells expressing the 5-HT$_{2Cser}$ variant receptor are obtained from human CSF and lysed with NP40, and the

13 isolated membranes are injected into rabbits. The lysed membranes are isolated in a non-ionic detergent so as not to affect the membrane bound receptors. Freund's adjuvant is used in the injection to help stimulate an antigenic response by the rabbits using well known methods. After two booster shots of the lysed membranes, the rabbits are bled and the sera isolated by centrifugation.

The antibodies in the crude rabbit sera extract are $^{125}$I labeled by well-known methods and tested for activity against transformed COS7 cells expressing the variant receptor. COS7 cells expressing the wildtype allele are used to preabsorb antibodies with nonspecific binding. A Western blot having one lane containing protein lysates from COS7 cells expressing the variant gene, and a second lane having lysates from COS7 cells expressing the wildtype 5-HT$_{2Ccys}$ receptor (control) is run.

Monoclonal antibodies can be made by well known methods in addition to the polyclonal antibodies discussed above. One method of producing monoclonal antibodies is discussed below.

These antibodies will specifically recognize the variant 5-HT$_{2Cser}$ receptor protein on cell membranes. Antibodies of this type can be used as research tools to characterize expression of this variant on different cells or in different populations or under different physiological conditions. Antibodies can further be used as a diagnostic of abnormal conditions linked to expression of the variant 5-HT$_{2Cser}$ receptor.

EXAMPLE 18

Production of Monoclonal Antibodies Against the 5-HT$_{2Cser}$ Variant Receptor Protein Cells expressing the 5-HT$_{2Cser}$ receptor are isolated from human CSF and lysed with NP40. The cell membranes are pelleted by centrifugation and isolated membranes having bound 5-HT$_{2Cser}$ variant receptor proteins are injected in Freunds adjuvant into mice. After being injected 9 times over a three week period, the mice spleens are removed and following conventional cell separation techniques were resuspended in PBS.

The suspended spleen cells are mixed (approximately 4:1) with SP 2/0 Myeloma cells. Polyethylene glycol is added to fuse the myeloma cells to the spleen cells, and the fused cells are selected in HAT media. The fused cells are aliquoted so that only one cell is grown in each well of a 96-well microtiter plate. Each cell is grown, the media removed and secreted proteins in the media are $^{125}$I or fluorescently labeled. The labeled media from each well is used to probe a Western blot of cell lysates having the 5-HT$_{2Cser}$ variant and the 5-HT$_{2Ccys}$ receptor. The desired fusion cell will produce a monoclonal antibody that strongly binds the 5-HT$_{2Cser}$ variant receptor lane on the Western blot, but doesn't bind to a similar sized protein in the 5-HT$_{2Ccys}$ (control) lane.

It will be appreciated by those skilled in the art that a monoclonal antibody that specifically recognizes the 5-HT$_{2Ccys}$ form of the receptor but does not recognize the variant 5-HT$_{2Cser}$ receptor could also be used for detection of presence of the variant. That is, such a monoclonal antibody would give a negative response with receptors from a homozygotic person for the 5-HT$_{2Cser}$ allele while giving a positive response with a 5-HT$_{2Ccys}$ control.

These monoclonal antibodies provide a way of detecting expression of the 5-HT$_{2Cser}$ variant serotonin receptor protein. Another method of detecting expression of the 5-HT$_{2Cser}$ variant is by in situ hybridization.

14

EXAMPLE 19

In Situ Hybridization Using 5-HT$_{2Cser}$ Variant Gene Fragments

In situ hybridization allows the identification of mRNA within intact tissues, including from human brain biopsies. In this method, oligonucleotides corresponding to a portion of the 5-HT$_{2Cser}$ variant gene (SEQ ID NO: 1) are used to detect specific mRNA species in the brain.

Biopsied brain tissue is perfused with a 4% formaldehyde solution using standard histology methods. The brain tissue is frozen with liquid nitrogen and cut into 5 μm to 30 μm sections that are placed on slides and incubated in proteinase K for approximately 15 minutes. The slides are then rinsed in diethylpyrocarbonate-treated water, and ethanol, and placed in a prehybridization buffer.

A radioactive probe corresponding to the PCR product obtained from using primers SEQ ID NO:3 and SEQ ID NO:4 (see Example 1) is made by performing the PCR using $[\alpha^{32}P]$ dCTP in the reaction mixture. The labeled PCR product is incubated with the sectioned brain tissue using standard hybridization methods. After incubation and washing at a temperature that allows binding to the 5-HT$_{2Cser}$ variant mRNA but not to the 5-HT$_{2Ccys}$ mRNA, the slides are air dried and labeled areas are visualized by autoradiography. Dark spots on the tissue sample indicate hybridization of the probe with the brain mRNA thereby demonstrating expression of the 5-HT$_{2Cser}$ variant receptor.

EXAMPLE 20

Site-directed Mutagenesis and Synthesis of mRNA

A human 5-HT$_{2C}$ receptor cDNA clone consisting of the entire coding region of the 5-HT$_{2C}$ receptor (Saltzman et al., *Biochem. Biophys. Res. Commun.* 181:1469, 1991) was subcloned into an pSP72 vector at EcoR1 and XbaII sites for mutagenesis. The single-base mutation that converts cysteine (encoded by TGT) to serine (encoded by TCT) in the resulting protein was introduced into the human 5-HT$_{2C}$ receptor cDNA at codon 23 by recombinant PCR (Vallette et al., *Nuc. Acid Res.* 17:723, 1989). The authenticity of the single base mutation was confirmed by double stranded DNA sequencing (United States Biochemical, Cleveland, Ohio). Complementary RNA was prepared by in vitro transcription using the mCAP™ kit from Stratagene (La Jolla, Calif.).

The mutated cDNA provided a ready source of mRNA specific for the 5-HT$_{2Cser}$ receptor. That mRNA as well as mRNA prepared from the cDNA encoding the 5-HT$_{2Ccys}$ receptor was expressed in oocytes isolated from the African clawed toad, *Xenopus laevis*. Following expression, the oocytes were tested for differences in ligand binding between the wildtype and allelic variant of the 5-HT$_{2C}$ receptor present on the oocytes' surface.

EXAMPLE 21

Oocyte Preparation, Oocyte Expression and Pharmacological Characterization of 5-HT$_{2Ccys}$ and 5-HT$_{2Cser}$ Using Electrophysiological Recording The oocytes were isolated from mature female *Xenopus laevis*. The follicular layer of the oocytes was removed by treatment with 0.2% collagenase A, and oocytes were transferred into a modified Barth's saline (MBS) solution containing: NaCl 88 mM, KCl 1 mM, NaHCO$_3$ 2.4 mM, Ca(NO$_3$)$_2$ 0.3 mM, CaCl$_2$ 0.9mM, MgSO$_4$ 0.8 mM, HEPES 10 mM (pH 7.5), to await mRNA or cRNA injection. Approximately 16–20 ng cRNA was injected per oocyte using a microinjection pump (World Precision Instruments, New Haven, Conn.). Between two and three days following oocyte cRNA microinjection, whole cell currents were measured in a perfusion medium MBS under two-electrode voltage-clamp at −70 mV. Serotonin was superfused at the rate of approximately 3 ml/min. for 30 seconds, with a period of 20 minutes between applications.

Figure 3A:
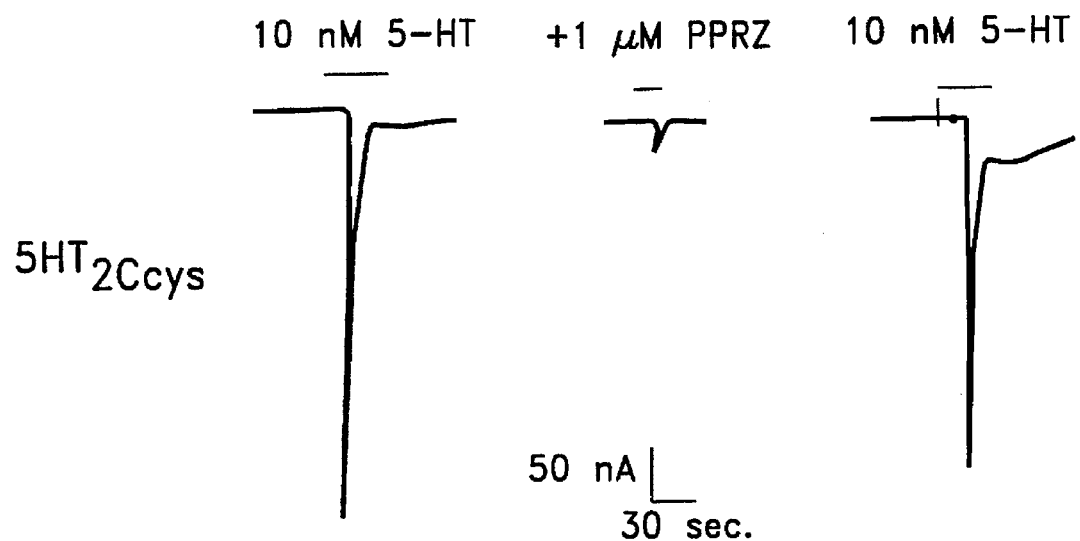
FIGS. 3A–B is a plot showing the relative current potentials activated by 10 nM 5-HT in oocytes expressing either 5-HT$_{2Cser}$ (FIG. 3B) or 5-HT$_{2Ccys}$ (FIG. 3A). 5-HT activated currents were suppressed in the presence of 1 µM 1-(1-naphthyl) piperazine HCL (PPRZ). The effect of PPRZ was reversible after a 20 min wash.
Figure 3B:
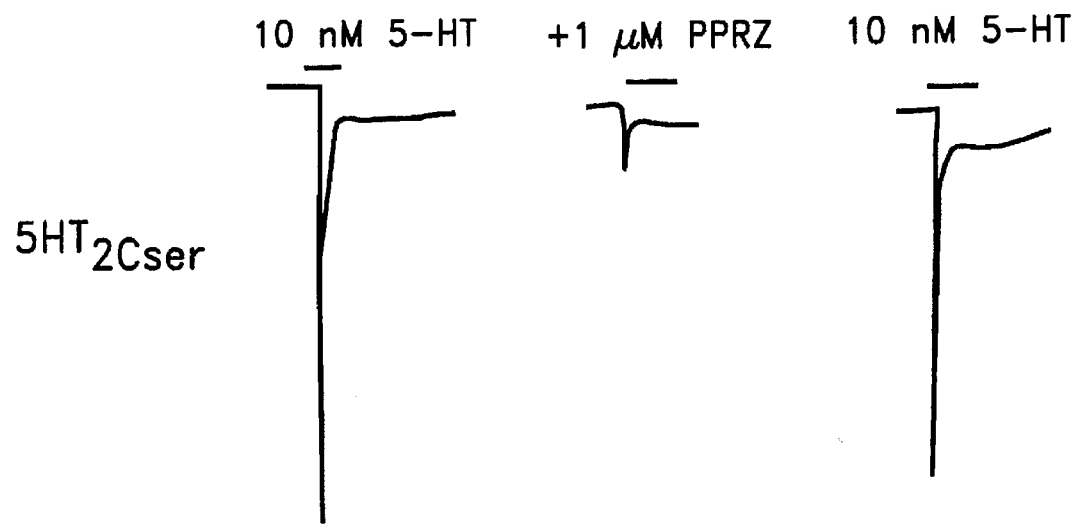

Xenopus oocytes have endogenous $Ca^{2+}$-activated chloride channels that can serve as a functional indicator for receptor-mediated inositoltriphosphate (IP3) increase. Taking advantage of this property, the oocyte expression system has been widely used to pharmacologically characterize $5-HT_{2C}$ function after microinjection of the synthetic receptor mRNA into oocytes (Julius et al., Science 241:558, 1988). We compared the electrophysiological properties of the human $5-HT_{2Ccys}$ and $5-HT_{2Cser}$ under identical conditions in oocytes expressing these receptors. As shown in FIG. 3, serotonin (5-HT) activated similar inward oscillating currents with a slow onset (3–10 sec) in oocytes expressing either $5-HT_{2Cser}$ or $5-HT_{2Ccys}$.

Figure 4:
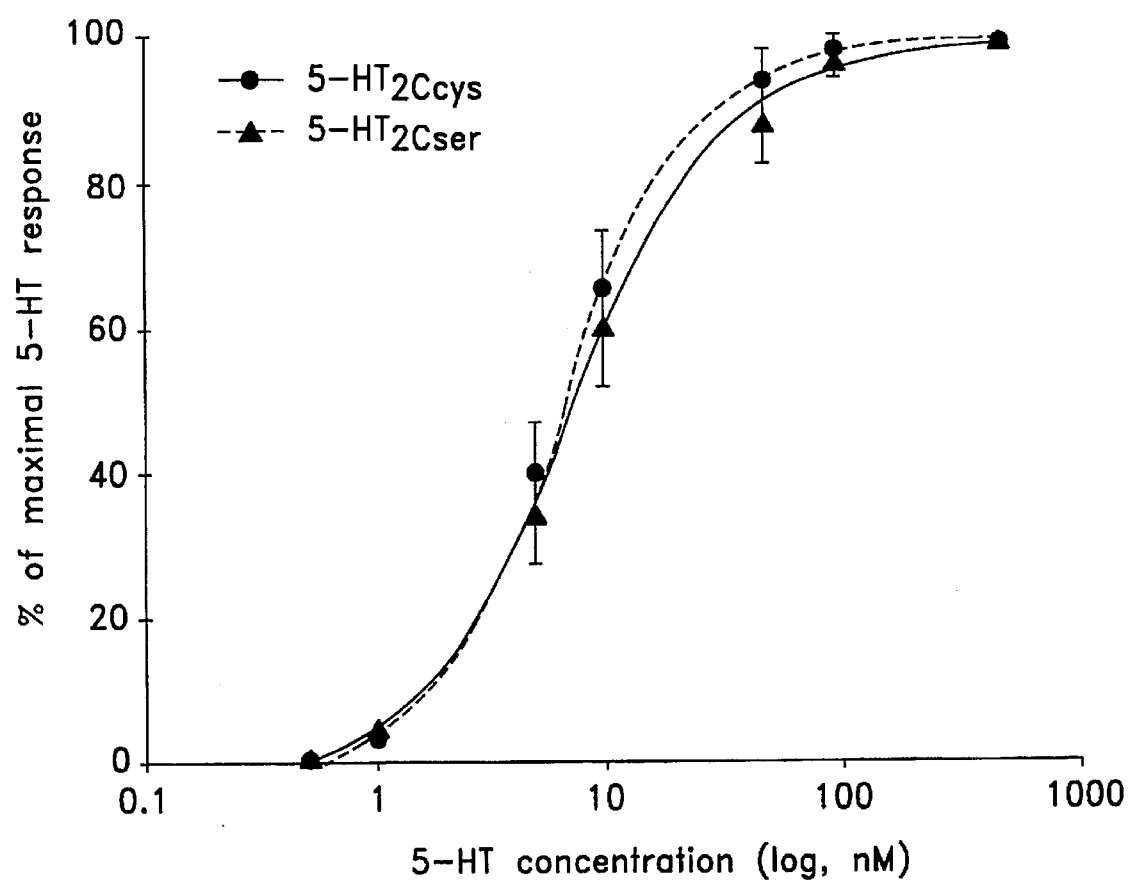
FIG. 4 is a dose-response curve for 5-HT activated currents in oocytes expressing either 5-HT$_{2Cccys}$ (●) or 5-HT$_{2Cser}$ (▲)

In agreement with others, we found that by allowing at least 20 min between the drug applications it was possible to achieve consistency in subsequent 5-HT-activated responses. The currents activated by 10 nM 5-HT were suppressed in the presence of 1 μM 1-(1-naphthyl) piperazine HCL (PPRZ), which is a selective antagonist for 5-ETNA and $5-HT_{2C}$ receptors. The effects of PPRZ on 5-HT-activated response for both types of receptors was reversible after a 20 min wash. A detectable inward current was activated by 1 nM 5-HT in cells expressing either $5-HT_{2Ccys}$ or $5-HT_{2Cser}$ receptors. The amplitude of 5-HT-activated currents increased in a concentration-dependent manner as agonist concentrations were increased from 1–500 nM (see FIG. 4). Similar maximal responses were obtained with 500 nM 5-HT in oocytes expressing either the $5-HT_{2Ccys}$ or $5-HT_{2Cser}$.

EXAMPLE 22

Ligand Binding to $5-HT_{2Ccys}$ and $5-HT_{2Cser}$ Receptors In Human Cells Cells expressing the $5-HT_{2Ccys}$ or $5-HT_{2Cser}$ receptors are isolated from human tissue, including from brain biopsies or cells isolated from CSF, using commonly known methods. The cells are incubated with known or suspected ligands for sufficient time and in sufficient concentrations to allow binding to the $5-HT_{2C}$ receptors, employing commonly used methods for determining binding in vitro. Known or suspected ligands include 5-HT analogs, 5-HT antagonists, and various pharmacological drugs used to treat neuropsychiatric disorders. Ligands are labeled either radioactively or fluorescently and relative binding of the ligand to the $5-HT_{2C}$ receptors is measured by measuring the amount of radioactivity or fluorescence attached to the membranes after the unbound fraction is washed away.

The relative binding efficiencies of ligands may be useful in developing new drugs to treat certain clinical conditions, or in determining effective drug dosages for clinical treatment of individuals with specific genotypes for the $5-HT_{2C}$ receptor.

EXAMPLE 23

Transfection of Mammalian Cells with the 5-ETacoy$_s$ and $5-HT_{2Cser}$ Receptor Genes Expression of the two forms of the $5-HT_{2C}$ serotonin receptor is assayed in mammalian COS7 cells transfected with the genes encoding the $5-HT_{2Ccys}$ or $5-HT_{2Cser}$ receptor proteins in an expression plasmid, pSRα. The $5-HT_{2Ccys}$ and $5-HT_{2Cser}$ genes individually are subcloned into the expression vector pSRα by using standard molecular cloning methods. The transfected COS7 cells are then placed in media for about 72 hours to allow expression of the $5-HT_{2Ccys}$ or $5-HT_{2Cser}$ receptors on their cell surface.

COS7 cells are transiently transfected with the pSRα-5-$HT_{2Ccys}$ or pSRα-5-$HT_{2Cser}$ construct using the calcium phosphate precipitation method as previously described by Monsma, F. J. et al., Proc. Natl. Acad. Sci. USA 87:6723, 1990. Cells are harvested 72 hours after transfection and either used directly or the membranes containing the $5-HT_{2C}$ receptors are isolated from the cells using methods described below.

Cells or membranes isolated from them are used to assay binding of various ligands of pharmacological interest. The relative binding efficiencies of ligands are useful in developing new drugs to treat clinical conditions associated with $5-HT_{2C}$ receptors.

While COS7 cells are a preferred embodiment, those skilled in the art will appreciate that other cells and vectors could be used in transfection for expression of the $5-HT_{2C}$ receptor genes.

EXAMPLE 24

Ligand Binding to Mammalian Cells Transfected with the $5-HT_{2Ccys}$ and $5-HT_{2Cser}$ receptor Genes Mammalian COS7 cells are transfected as described above, and binding of ligands to the $5-HT_{2Ccys}$ or $5-HT_{2Cser}$ serotonin receptors is assayed using whole cells expressing the $5-HT_{2Ccys}$ or $5-HT_{2Cser}$ receptors on their surface.

Cells are collected 72 hours after transfection and placed in fresh media containing radiolabeled or fluorescently labeled ligands. Ligands include 5-HT analogs, 5-HT antagonists, and various pharmacological drugs used to treat neuropsychiatric disorders. After incubation for various times to allow binding of the ligands to the $5-HT_{2C}$ receptors, cells are washed and then assayed for binding of the ligand to the cells, employing commonly used methods for detecting radioactivity or fluorescence.

This method is useful because cells that express $5-HT_{2C}$ receptors can be obtained with relative ease without relying on clinical samples. Mammalian COS7 cells probably reflect the physiological conditions normally affecting expression of serotonin receptors in humans. The relative binding efficiencies of ligands are useful in developing new drugs to treat clinical conditions associated with $5-HT_{2C}$ receptors, or in determining effective drug dosages for clinical treatment of individuals with specific genotypes for the $5-HT_{2C}$ receptor.

EXAMPLE 25

Ligand Binding to Membranes Isolated from Mammalian Cells Transfected with the $5-HT_{2Ccys}$ and $5-HT_{2Cser}$ Receptor Genes Mammalian COS7 cells are transfected as described above, and binding of ligands to the $5-HT_{2Ccys}$ or $5-HT_{2Cser}$ serotonin receptors is assayed using membranes isolated from cells expressing the $5-HT_{2Ccys}$ or $5-HT_{2Cser}$ receptors on their surface. Cells are harvested 72 hours after transfection and either disrupted in a dounce homogenizer in 50 mM Tris-HCl, pH at 37° C., 10mM $MgSO_4$ and 0.5 mM EDTA, or frozen in 5 mM Tris-HCl, pH 7.4 at 25° C., 5mM MgCl₂, 250 mM sucrose and stored in liquid N₂ prior to membrane preparation. Crude membranes were prepared from cell homogenates by centrifugation at 43,000×g, and re-suspension in homogenization buffer at a protein concentration of 60 µg/ml.

Once the crude membranes are prepared from the cell homogenates, screening of various pharmacologically indicated ligands for differential binding to the 5-HT$_{2C}$ receptors is performed as discussed above. Ligands, which are radiolabeled or fluorescently labeled, include 5-HT analogs, 5-HT antagonists, and various pharmacological drugs used to treat neuropsychiatric disorders.

This method is useful because it provides a ready source of serotonin receptors expressed on mammalian cells for comparison of many different ligands, alone or in combination, under identical binding conditions. The information from the assay relating to relative binding efficiencies of ligands is useful in developing new drugs to treat certain clinical conditions associated with expression of the different forms of the 5-HT$_{2C}$ receptor.

The relevant portions of the articles cited herein are incorporated by reference.

We claim:

1. An isolated DNA sequence that codes for an allelic variant of the serotonin 5HT2C receptor having the sequence of SEQ ID NO: 2.

2. A vector containing the isolated DNA of claim 1.

3. Host cells coming the vector of claim 2.

4. The isolated DNA of claim 1 wherein said DNA has the nucleic acid sequence of SEQ ID NO:1.

5. A method for detecting the presence of DNA that codes for a 5HT2C$_{Ser}$ allelic variant comprising:

(a) providing a sample of human DNA;

(b) amplifying said DNA with primers capable of amplifying exon 2 of the human 5HT$_2$C$_{Ser}$ gene; and (c) detecting whether the sequence of the amplified DNA corresponds to that of the human 5HT2C$_{Ser}$ gene in which a guanine to cytosine genetic transversion converts a cysteine codon to a serine codon.

6. The method of claim 5 wherein said amplifying step comprises polymerase chain reaction amplification.

7. The method of claim 6 wherein said amplification uses DNA primers that create a new restriction site when said 5HT2C$_{Ser}$ gene is present in the amplified DNA.

8. The method of claim 7 wherein said restriction site is cleaved by HinfI.

9. The method of claim 7 wherein said DNA primers are SEQ ID NOS: 5 and 6.

10. The method of claim 5 wherein said detecting step further comprises restriction enzyme digestion followed by gel electrophoresis.

11. The method of claim 10 wherein said restriction enzyme is Rsa I.

12. The method of claim 10 wherein said gel electrophorresis is on a Mutation Detection Enhancement gel.

13. The method of claim 5 wherein said detecting step includes denaturation of said DNA.

14. The method of claim 5 wherein said detecting step further comprises nucleic acid sequencing of the amplified DNA.

15. The method of claim 5 wherein step (c) comprises comparing the amplified region of DNA to SEQ ID NO:1.

16. The method of claim 5 wherein step (c) comprises comparing the sequence of the protein encoded by the amplified region to SEQ ID NO:2.

* * * * *

UNITED STATES PATENT AND TRADEMARK OFFICE
CERTIFICATE OF CORRECTION

PATENT NO. : 5,654,139
DATED : August 5, 1997
INVENTOR(S) : Jaakko Lappalainen; Markku Linnoila; David Goldman It is certified that error appears in the above-identified patent and that said Letters Patent is hereby corrected as shown below:

On the title page, item [73] Assignee, reads:
"The United States of America as represented by the Department of Health and Human Services, Washington, D.C." and should read as in the Patent, [73] Assignee as follows
-- The United States of America, as represented by the Secretary, Department of Health and Human Services, Rockville, MD --.

Column 27, line 19, claim 3 should read:

-- Host cells containing the vector of claim 2. --

Signed and Sealed this

Twenty-seventh Day of January, 1998

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2733 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( i x ) FEATURE:
        ( A ) NAME/KEY: Coding Sequence
        ( B ) LOCATION: 788...2164
        ( D ) OTHER INFORMATION:

( x i ) SEQUENCE DESCRIPTION: SEQ ID NO:1:

```
GAATTCGGGA  GCGTCCTCAG  ATGCACCGAT  CTTCCCGATA  CTGCCTTTGG  AGCGGCTAGA      60

TTGCTAGCCT  TGGCTGCTCC  ATTGGCCTGC  CTTGCCCCTT  ACCTGCCGAT  TGCATATGAA     120

CTCTTCTTCT  GTCTGTACAT  CGTTGTCGTC  GGAGTCGTCG  CGATCGTCGT  GGCGCTCGTG     180

TGATGGCCTT  CGTCCGTTTA  GAGTAGTGTA  GTTAGTTAGG  GGCCAACGAA  GAAGAAAGAA     240

GACGCGATTA  GTGCAGAGAT  GCTGGAGGTG  GTCAGTTACT  AAGCTAGAGT  AAGATAGCGG     300

AGCGAAAAGA  GCCAAACCTA  GCCGGGGGGC  GCACGGTCAC  CCAAAGGAGG  TCGACTCGCC     360

GGCGCTTCCT  ATCGCGCCGA  GCTCCCTCCA  TTCCTCTCCC  TCCGCCGAGG  CGCGAGGTTG     420

CGGCGCGCAG  CGCAGCGCAG  CTCAGCGCAC  CGACTGCCGC  GGGCTCCGCT  GGGCGATTGC     480

AGCCGAGTCC  GTTTCTCGTC  TAGCTGCCGC  CGCGGCGACC  GCTGCCTGGT  CTTCCTCCCG     540

GACGCTAGTG  GGTTATCAGC  TAACACCCGC  GAGCATCTAT  AACATAGGCC  AACTGACGCC     600

ATCCTTCAAA  AACAACTGTC  TGGGAAAAAA  AGAATAAAAA  GTAGTGTGAG  AGCAGAAAAC     660

GTGATTGAAA  CACGACCAAT  CTTTCTTCAG  TGCCAAAGGG  TGGAAAAGAA  AGGATGATAT     720

GATGAACCTA  GCCTGTTAAT  TTCGTCTTCT  CAATTTTAAA  CTTTGGTTGC  TTAAGACTGA     780

AGCAATC ATG GTG AAC CTG AGG AAT GCG GTG CAT TCA TTC CTT GTG CAC          829
               Met Val Asn Leu Arg Asn Ala Val His Ser Phe Leu Val His
                1               5                  10
```

-continued

| | | | | | | | | | | | | | | | | |
|---|---|---|---|---|---|---|---|---|---|---|---|---|---|---|---|---|
| CTA | ATT | GGC | CTA | TTG | GTT | TGG | CAA | TCT | GAT | ATT | TCT | GTG | AGC | CCA | GTA | 877 |
| Leu | Ile | Gly | Leu | Leu | Val | Trp | Gln | Ser | Asp | Ile | Ser | Val | Ser | Pro | Val | |
| 15 | | | | 20 | | | | | 25 | | | | | | 30 | |
| GCA | GCT | ATA | GTA | ACT | GAC | ATT | TTC | AAT | ACC | TCC | GAT | GGT | GGA | CGC | TTC | 925 |
| Ala | Ala | Ile | Val | Thr | Asp | Ile | Phe | Asn | Thr | Ser | Asp | Gly | Gly | Arg | Phe | |
| | | | | 35 | | | | | 40 | | | | | 45 | | |
| AAA | TTC | CCA | GAC | GGG | GTA | CAA | AAC | TGG | CCA | GCA | CTT | TCA | ATC | GTC | ATC | 973 |
| Lys | Phe | Pro | Asp | Gly | Val | Gln | Asn | Trp | Pro | Ala | Leu | Ser | Ile | Val | Ile | |
| | | | 50 | | | | | 55 | | | | | 60 | | | |
| ATA | ATA | ATC | ATG | ACA | ATA | GGT | GGC | AAC | ATC | CTT | GTG | ATC | ATG | GCA | GTA | 1021 |
| Ile | Ile | Ile | Met | Thr | Ile | Gly | Gly | Asn | Ile | Leu | Val | Ile | Met | Ala | Val | |
| | | 65 | | | | 70 | | | | | 75 | | | | | |
| AGC | ATG | GAA | AAG | AAA | CTG | CAC | AAT | GCC | ACC | AAT | TAC | TTC | TTA | ATG | TCC | 1069 |
| Ser | Met | Glu | Lys | Lys | Leu | His | Asn | Ala | Thr | Asn | Tyr | Phe | Leu | Met | Ser | |
| | 80 | | | | | 85 | | | | | 90 | | | | | |
| CTA | GCC | ATT | GCT | GAT | ATG | CTA | GTG | GGA | CTA | CTT | GTC | ATG | CCC | CTG | TCT | 1117 |
| Leu | Ala | Ile | Ala | Asp | Met | Leu | Val | Gly | Leu | Leu | Val | Met | Pro | Leu | Ser | |
| 95 | | | | | 100 | | | | | 105 | | | | | 110 | |
| CTC | CTG | GCA | ATC | CTT | TAT | GAT | TAT | GTC | TGG | CCA | CTA | CCT | AGA | TAT | TTG | 1165 |
| Leu | Leu | Ala | Ile | Leu | Tyr | Asp | Tyr | Val | Trp | Pro | Leu | Pro | Arg | Tyr | Leu | |
| | | | | 115 | | | | | 120 | | | | | 125 | | |
| TGC | CCC | GTC | TGG | ATT | TCT | TTA | GAT | GTT | TTA | TTT | TCA | ACA | GCG | TCC | ATC | 1213 |
| Cys | Pro | Val | Trp | Ile | Ser | Leu | Asp | Val | Leu | Phe | Ser | Thr | Ala | Ser | Ile | |
| | | | 130 | | | | | 135 | | | | | 140 | | | |
| ATG | CAC | CTC | TGC | GCT | ATA | TCG | CTG | GAT | CGG | TAT | GTA | GCA | ATA | CGT | AAT | 1261 |
| Met | His | Leu | Cys | Ala | Ile | Ser | Leu | Asp | Arg | Tyr | Val | Ala | Ile | Arg | Asn | |
| | | 145 | | | | 150 | | | | | 155 | | | | | |
| CCT | ATT | GAG | CAT | AGC | CGT | TTC | AAT | TCG | CGG | ACT | AAG | GCC | ATC | ATG | AAG | 1309 |
| Pro | Ile | Glu | His | Ser | Arg | Phe | Asn | Ser | Arg | Thr | Lys | Ala | Ile | Met | Lys | |
| | 160 | | | | | 165 | | | | | 170 | | | | | |
| ATT | GCT | ATT | GTT | TGG | GCA | ATT | TCT | ATA | GGT | GTA | TCA | GTT | CCT | ATC | CCT | 1357 |
| Ile | Ala | Ile | Val | Trp | Ala | Ile | Ser | Ile | Gly | Val | Ser | Val | Pro | Ile | Pro | |
| 175 | | | | | 180 | | | | | 185 | | | | | 190 | |
| GTG | ATT | GGA | CTG | AGG | GAC | GAA | GAA | AAG | GTG | TTC | GTG | AAC | AAC | ACG | ACG | 1405 |
| Val | Ile | Gly | Leu | Arg | Asp | Glu | Glu | Lys | Val | Phe | Val | Asn | Asn | Thr | Thr | |
| | | | | 195 | | | | | 200 | | | | | 205 | | |
| TGC | GTG | CTC | AAC | GAC | CCA | AAT | TTC | GTT | CTT | ATT | GGG | TCC | TTC | GTA | GCT | 1453 |
| Cys | Val | Leu | Asn | Asp | Pro | Asn | Phe | Val | Leu | Ile | Gly | Ser | Phe | Val | Ala | |
| | | | 210 | | | | | 215 | | | | | 220 | | | |
| TTC | TTC | ATA | CCG | CTG | ACG | ATT | ATG | GTG | ATT | ACG | TAT | TGC | CTG | ACC | ATC | 1501 |
| Phe | Phe | Ile | Pro | Leu | Thr | Ile | Met | Val | Ile | Thr | Tyr | Cys | Leu | Thr | Ile | |
| | | 225 | | | | 230 | | | | | 235 | | | | | |
| TAC | GTT | CTG | CGC | CGA | CAA | GCT | TTG | ATG | TTA | CTG | CAC | GGC | CAC | ACC | GAG | 1549 |
| Tyr | Val | Leu | Arg | Arg | Gln | Ala | Leu | Met | Leu | Leu | His | Gly | His | Thr | Glu | |
| | 240 | | | | | 245 | | | | | 250 | | | | | |
| GAA | CCG | CCT | GGA | CTA | AGT | CTG | GAT | TTC | CTG | AAG | TGC | TGC | AAG | AGG | AAT | 1597 |
| Glu | Pro | Pro | Gly | Leu | Ser | Leu | Asp | Phe | Leu | Lys | Cys | Cys | Lys | Arg | Asn | |
| 255 | | | | | 260 | | | | | 265 | | | | | 270 | |
| ACG | GCC | GAG | GAA | GAG | AAC | TCT | GCA | AAC | CCT | AAC | CAA | GAC | CAG | AAC | GCA | 1645 |
| Thr | Ala | Glu | Glu | Glu | Asn | Ser | Ala | Asn | Pro | Asn | Gln | Asp | Gln | Asn | Ala | |
| | | | | 275 | | | | | 280 | | | | | 285 | | |
| CGC | CGA | AGA | AAG | AAG | AAG | GAG | AGA | CGT | CCT | AGG | GGC | ACC | ATG | CAG | GCT | 1693 |
| Arg | Arg | Arg | Lys | Lys | Lys | Glu | Arg | Arg | Pro | Arg | Gly | Thr | Met | Gln | Ala | |
| | | | | 290 | | | | | 295 | | | | | 300 | | |
| ATC | AAC | AAT | GAA | AGA | AAA | GCT | TCG | AAA | GTC | CTT | GGG | ATT | GTT | TTC | TTT | 1741 |
| Ile | Asn | Asn | Glu | Arg | Lys | Ala | Ser | Lys | Val | Leu | Gly | Ile | Val | Phe | Phe | |
| | | 305 | | | | | 310 | | | | | 315 | | | | |
| GTG | TTT | CTG | ATC | ATG | TGG | TGC | CCA | TTT | TTC | ATT | ACC | AAT | ATT | CTG | TCT | 1789 |
| Val | Phe | Leu | Ile | Met | Trp | Cys | Pro | Phe | Phe | Ile | Thr | Asn | Ile | Leu | Ser | |
| | 320 | | | | | 325 | | | | | 330 | | | | | |

-continued

```
GTT CTT TGT GAG AAG TCC TGT AAC CAA AAG CTC ATG GAA AAG CTT CTG    1837
Val Leu Cys Glu Lys Ser Cys Asn Gln Lys Leu Met Glu Lys Leu Leu
335             340                 345                 350

AAT GTG TTT GTT TGG ATT GGC TAT GTT TGT TCA GGA ATC AAT CCT CTG    1885
Asn Val Phe Val Trp Ile Gly Tyr Val Cys Ser Gly Ile Asn Pro Leu
                355                 360                 365

GTG TAT ACT CTG TTC AAC AAA ATT TAC CGA AGG GCA TTC TCC AAC TAT    1933
Val Tyr Thr Leu Phe Asn Lys Ile Tyr Arg Arg Ala Phe Ser Asn Tyr
            370                 375                 380

TTG CGT TGC AAT TAT AAG GTA GAG AAA AAG CCT CCT GTC AGG CAG ATT    1981
Leu Arg Cys Asn Tyr Lys Val Glu Lys Lys Pro Pro Val Arg Gln Ile
        385                 390                 395

CCA AGA GTT GCC GCC ACT GCT TTG TCT GGG AGG GAG CTT AAT GTT AAC    2029
Pro Arg Val Ala Ala Thr Ala Leu Ser Gly Arg Glu Leu Asn Val Asn
    400                 405                 410

ATT TAT CGG CAT ACC AAT GAA CCG GTG ATC GAG AAA GCC AGT GAC AAT    2077
Ile Tyr Arg His Thr Asn Glu Pro Val Ile Glu Lys Ala Ser Asp Asn
415                 420                 425                 430

GAG CCC GGT ATA GAG ATG CAA GTT GAG AAT TTA GAG TTA CCA GTA AAT    2125
Glu Pro Gly Ile Glu Met Gln Val Glu Asn Leu Glu Leu Pro Val Asn
                435                 440                 445

CCC TCC AGT GTG GTT AGC GAA AGG ATT AGC AGT GTG TGA GAAAGAACAG CAC 2177
Pro Ser Ser Val Val Ser Glu Arg Ile Ser Ser Val *
            450                 455

AGTCTTTCT ACGGTACAAG CTACATATGT AGGAAAATTT TCTTCTTTAA TTTTTCTGTT    2237
GGTCTTAACT AATGTAAATA TTGCTGTCTG AAAAAGTGTT TTTACATATA GCTTTGCAAC   2297
CTTGTACTTT ACAATCATGC CTACATTAGT GAGATTTAGG GTTCTATATT TACTGTTTAT   2357
AATAGGTGGA GACTAACTTA TTTTGATTGT TGATGAATA  AAATGTTTAT TTTTGCTCTC   2417
CCTCCCTTCT TTCCTTCCTT TTTTCCTTTC TTCCTTCCTT TCTCTCTTTC TTTTGTGCAT   2477
ATGGCAACGT TCATGTTCAT CTCAGGTGGC ATTTGCAGGT GACCAGAATG AGGCACATGA   2537
CAGTGGTTAT ATTTCAACCA CACCTAAATT AACAAATTCA GTGGACATTT GTTCTGGGTT   2597
AACAGTAAAT ATACACTTTA CATTCTTGCT CTGCTCATCT ACACATATAA ACACAGTAAG   2657
ATAGGTTCTG CTTTCTGATA CATCTGTCAG TGAGTCAGAG GCAGAACCTA GTCTTGTTGT   2717
TCATATAGGG GAATTC                                                  2733
```

( 2 ) INFORMATION FOR SEQ ID NO:2:

( i ) SEQUENCE CHARACTERISTICS:
        ( A ) LENGTH: 458 amino acids
        ( B ) TYPE: amino acids
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:

( x i ) SEQUENCE DESCRIPTION: SEQ ID NO:2:

```
Met Val Asn Leu Arg Asn Ala Val His Ser Phe Leu Val His Leu Ile
 1               5                  10                  15

Gly Leu Leu Val Trp Gln Ser Asp Ile Ser Val Ser Pro Val Ala Ala
            20                  25                  30

Ile Val Thr Asp Ile Phe Asn Thr Ser Asp Gly Gly Arg Phe Lys Phe
```

|  |  | 35 |  |  |  |  | 40 |  |  |  |  | 45 |  |  |  |
|---|---|---|---|---|---|---|---|---|---|---|---|---|---|---|---|
| Pro | Asp<br>50 | Gly | Val | Gln | Asn | Trp<br>55 | Pro | Ala | Leu | Ser | Ile<br>60 | Val | Ile | Ile | Ile |
| Ile<br>65 | Met | Thr | Ile | Gly<br>70 | Gly | Asn | Ile | Leu | Val | Ile<br>75 | Met | Ala | Val | Ser | Met<br>80 |
| Glu | Lys | Lys | Leu | His<br>85 | Asn | Ala | Thr | Asn | Tyr<br>90 | Phe | Leu | Met | Ser | Leu<br>95 | Ala |
| Ile | Ala | Asp | Met<br>100 | Leu | Val | Gly | Leu | Leu<br>105 | Val | Met | Pro | Leu | Ser<br>110 | Leu | Leu |
| Ala | Ile | Leu<br>115 | Tyr | Asp | Tyr | Val | Trp<br>120 | Pro | Leu | Pro | Arg<br>125 | Tyr | Leu | Cys | Pro |
| Val | Trp<br>130 | Ile | Ser | Leu | Asp<br>135 | Val | Leu | Phe | Ser | Thr<br>140 | Ala | Ser | Ile | Met | His |
| Leu<br>145 | Cys | Ala | Ile | Ser | Leu<br>150 | Asp | Arg | Tyr | Val | Ala<br>155 | Ile | Arg | Asn | Pro | Ile<br>160 |
| Glu | His | Ser | Arg | Phe<br>165 | Asn | Ser | Arg | Thr | Lys<br>170 | Ala | Ile | Met | Lys | Ile<br>175 | Ala |
| Ile | Val | Trp | Ala<br>180 | Ile | Ser | Ile | Gly | Val<br>185 | Ser | Val | Pro | Ile | Pro<br>190 | Val | Ile |
| Gly | Leu | Arg<br>195 | Asp | Glu | Glu | Lys | Val<br>200 | Phe | Val | Asn | Asn | Thr<br>205 | Thr | Cys | Val |
| Leu | Asn<br>210 | Asp | Pro | Asn | Phe | Val<br>215 | Leu | Ile | Gly | Ser | Phe<br>220 | Val | Ala | Phe | Phe |
| Ile<br>225 | Pro | Leu | Thr | Ile | Met<br>230 | Val | Ile | Thr | Tyr | Cys<br>235 | Leu | Thr | Ile | Tyr | Val<br>240 |
| Leu | Arg | Arg | Gln | Ala<br>245 | Leu | Met | Leu | Leu | His<br>250 | Gly | His | Thr | Glu | Glu<br>255 | Pro |
| Pro | Gly | Leu | Ser<br>260 | Leu | Asp | Phe | Leu | Lys<br>265 | Cys | Cys | Lys | Arg | Asn<br>270 | Thr | Ala |
| Glu | Glu | Glu<br>275 | Asn | Ser | Ala | Asn | Pro<br>280 | Asn | Gln | Asp | Gln | Asn<br>285 | Ala | Arg | Arg |
| Arg | Lys<br>290 | Lys | Lys | Glu | Arg | Arg<br>295 | Pro | Arg | Gly | Thr | Met<br>300 | Gln | Ala | Ile | Asn |
| Asn<br>305 | Glu | Arg | Lys | Ala | Ser<br>310 | Lys | Val | Leu | Gly | Ile<br>315 | Val | Phe | Phe | Val | Phe<br>320 |
| Leu | Ile | Met | Trp | Cys<br>325 | Pro | Phe | Phe | Ile | Thr<br>330 | Asn | Ile | Leu | Ser | Val<br>335 | Leu |
| Cys | Glu | Lys | Ser<br>340 | Cys | Asn | Gln | Lys | Leu<br>345 | Met | Glu | Lys | Leu | Leu<br>350 | Asn | Val |
| Phe | Val | Trp<br>355 | Ile | Gly | Tyr | Val | Cys<br>360 | Ser | Gly | Ile | Asn | Pro<br>365 | Leu | Val | Tyr |
| Thr | Leu<br>370 | Phe | Asn | Lys | Ile | Tyr<br>375 | Arg | Arg | Ala | Phe | Ser<br>380 | Asn | Tyr | Leu | Arg |
| Cys<br>385 | Asn | Tyr | Lys | Val | Glu<br>390 | Lys | Lys | Pro | Pro | Val<br>395 | Arg | Gln | Ile | Pro | Arg<br>400 |
| Val | Ala | Ala | Thr | Ala<br>405 | Leu | Ser | Gly | Arg | Glu<br>410 | Leu | Asn | Val | Asn | Ile<br>415 | Tyr |
| Arg | His | Thr | Asn | Glu<br>420 | Pro | Val | Ile | Glu<br>425 | Lys | Ala | Ser | Asp | Asn<br>430 | Glu | Pro |
| Gly | Ile | Glu | Met<br>435 | Gln | Val | Glu | Asn | Leu<br>440 | Glu | Leu | Pro | Val<br>445 | Asn | Pro | Ser |
| Ser | Val<br>450 | Val | Ser | Glu | Arg | Ile<br>455 | Ser | Ser | Val |  |  |  |  |  |  |

( 2 ) INFORMATION FOR SEQ ID NO:3:

( i ) SEQUENCE CHARACTERISTICS:
    ( A ) LENGTH: 20 amino acids
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

```
CACCTAATTG GCCTATTGGT T                                                 21
```

( 2 ) INFORMATION FOR SEQ ID NO:4:

( i ) SEQUENCE CHARACTERISTICS:
    ( A ) LENGTH: 20 amino acids
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:4:

```
AAGGATTGCC AGGAGAGACA G                                                 21
```

( 2 ) INFORMATION FOR SEQ ID NO:5:

( i ) SEQUENCE CHARACTERISTICS:
    ( A ) LENGTH: 20 amino acids
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:5:

```
TTGGCCTATT GGTTTGGGAA T                                                 21
```

( 2 ) INFORMATION FOR SEQ ID NO:6:

( i ) SEQUENCE CHARACTERISTICS:
    ( A ) LENGTH: 22 amino acids
    ( B ) TYPE: nucleic acid
    ( C ) STRANDEDNESS: single
    ( D ) TOPOLOGY: linear ( i i ) MOLECULE TYPE: cDNA -continued (iii) HYPOTHETICAL: NO (iv) ANTI-SENSE: NO (v) FRAGMENT TYPE:

(vi) ORIGINAL SOURCE:

(xi) SEQUENCE DESCRIPTION: SEQ ID NO:6:

GTCTGGGAAT TTGAAGCGTC CAC    23